United States Patent [19]

Miura

[11] Patent Number: 5,167,500
[45] Date of Patent: Dec. 1, 1992

[54] ORTHODONTIC APPLIANCE
[75] Inventor: Fujio Miura, Sakae, Japan
[73] Assignee: GAC International, Inc., Central Islip, N.Y.
[21] Appl. No.: 719,774
[22] Filed: Jun. 24, 1991
[30] Foreign Application Priority Data Jun. 25, 1990 [JP] Japan ................................. 2-66028

[51] Int. Cl.⁵ .............................................. A61C 7/00
[52] U.S. Cl. ...................................................... 433/7
[58] Field of Search ................... 433/7, 18, 20, 22, 21

[56] References Cited

U.S. PATENT DOCUMENTS

| 360,695 | 4/1887 | Holmes | 433/7 |
|---|---|---|---|
| 3,284,902 | 11/1966 | Dillberg et al. | 433/7 |
| 4,037,324 | 7/1977 | Andreasen | 32/14 |
| 4,323,345 | 4/1982 | Wallshein | 433/7 |
| 4,490,112 | 12/1984 | Tanaka et al. | 433/20 |
| 4,571,177 | 2/1986 | Dahan | 433/7 |
| 4,849,032 | 7/1989 | Kawaguchi | 148/11.5 R |

FOREIGN PATENT DOCUMENTS 1566260 2/1979 Fed. Rep. of Germany .......... 433/7
986642 8/1951 France ..................................... 433/7

OTHER PUBLICATIONS

"American Journal of Orthodontics and Dentofacial Orthopedics", vol. 94, No. 2, pp. 89-96, Aug. 1988.
"American Journal of Orthodontics and Dentofacial Orthopedics", vol. 90, No. 1, pp. 1-10, Jul. 1986.

Primary Examiner—Cary E. O'Connor
Attorney, Agent, or Firm—Kenyon & Kenyon

[57] ABSTRACT

An orthodontic appliance having a pair of bases supported by guides so as to be capable of opening and closing. A memory alloy coil spring having superelastic properties is mounted between the pair of bases. The appliance is constructed so that the spring pressure of the superelastic memory alloy coil spring transmits to the tooth or the jaw bone as orthodontic force by means of the opening and closing of the pair of bases.

17 Claims, 5 Drawing Sheets 5,167,500

ORTHODONTIC APPLIANCE

BACKGROUND OF THE INVENTION

1. Field of the Invention

The present invention is within the field of orthodontics and relates to an improvement in an orthodontic appliance used for expansion of a patient's dental arch or upper jaw bone and alveolar shifting of teeth.

2. Description of Related Art

Known orthodontic devices as shown in FIG. 7, are constructed so that bases 1 and 2, supported by two right-left guide rods 3, are capable of opening and closing. A threaded rod 4 having reversed threads is screwed into the central parts of the bases 1 and 2 so that the pair of bases 1 and 2 can be made to approach or separate on guide rods 3 by rotating operating part 4a of the threaded rod 4 with tool 5.

When using this orthodontic appliance in clinical practice for expansion of the upper jaw bone, as shown in FIG. 8, the pair of bases 1 and 2 are soldered to each connecting arm 6a of fixed type expansion apparatus 6, and after attaching the sides of bases 6b of expansion apparatus 6 to tooth surfaces T by means of adhesive or bands (not illustrated), threaded rod 4 is rotated in a prescribed direction by means of tool 5. When each base 1 and 2 shifts away from one another, the dental arch of the patient expands from the orthodontic force obtained by the shifting, and it becomes possible to expand the upper jaw bone by diastematic stitching of the palate.

When used in clinical alveolar shifting of tooth T1, as shown in FIG. 9, the embedded pair of bases 1 and 2 are connected between fixed side bed 7a and shifting side bed 7b of removable bed apparatus 7. Fixed side bed 7a is attached to the side of normal teeth T2 by means of clasp 8, and after attaching shifting side bed 7b to tooth T1 that requires treatment by means of clasp 8, threaded rod 4 of the orthodontic appliance is rotated in a prescribed direction in the same manner as before. Thus, when each base 1 and 2 shifts in the opening direction, it becomes possible to shift tooth T1 in the prescribed direction by the orthodontic force obtained from such shifting.

Such prior orthodontic appliances attempt to obtain their orthodontic force by the shifting of base 1 that accompanies the rotation of threaded rod 4 during expansion of the upper jaw bone and during shifting of teeth. Because of this, when the expansion of the upper jaw bone and the shifting of teeth advance in the course of treatment, it becomes necessary to separate the pair of bases 1 and 2 gradually by repeated rotations of threaded rod 4 in order to obtain the orthodontic force required at each time. Because the adjustments in orthodontic force must be ultimately done by the shifting of bases 1 and 2 that accompanies the rotation of threaded rod 4, there is difficulty in applying the ideal orthodontic force because each adjustment is imparted as a displacement rather than as a force.

Furthermore, these adjustments of the orthodontic appliance are not always made by specialists in orthodontics, and in some instances must be made by the patient or by a person caring for the patient. In these cases, the above described adjustment problem becomes more pronounced.

Consequently, it is difficult to properly adjust the force when mechanically shifting the pair of bases 1 and 2 of known orthodontic appliances to displace them by means of rotation of threaded rod 4.

Accordingly, it is an object of the present invention to provide an orthodontic appliance which reduces or eliminates the need for periodic adjustments in orthodontic force during treatment.

It is a further object of the invention to provide an orthodontic appliance which is capable of exerting a substantially constant orthodontic force continuously to teeth.

SUMMARY OF THE INVENTION

The orthodontic appliance of the present invention overcomes the problems described above. The orthodontic appliance includes a pair of bases supported by guide members so as to be capable of opening and closing. A memory alloy coil spring having superelastic properties is mounted between the pair of bases. The superelastic coil spring is constructed so that its spring pressure transmits to the tooth or the jaw bone suitable orthodontic force by means of the opening and closing of the pair of bases.

DETAILED DESCRIPTION OF THE INVENTION

Figure 1:
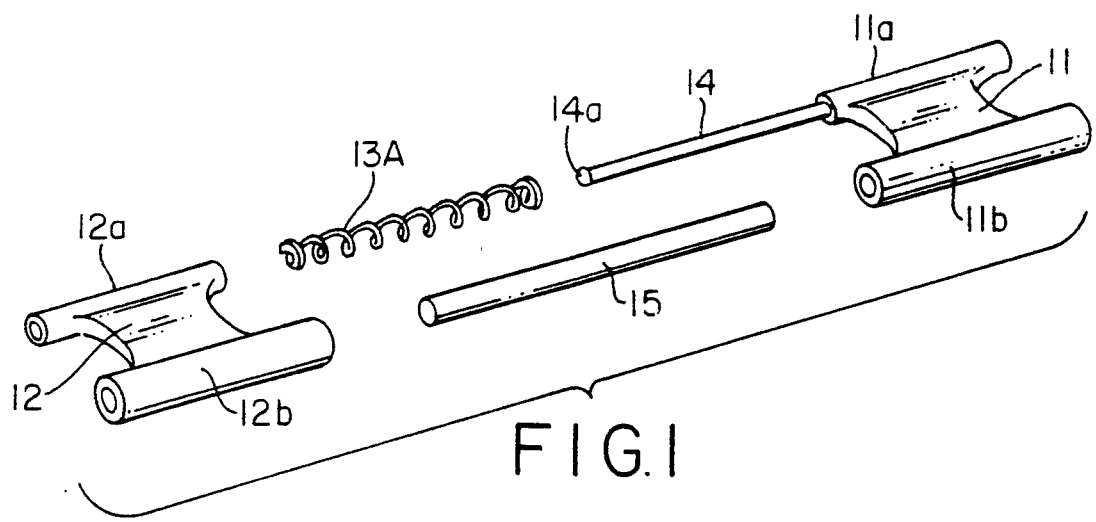
FIG. 1 is an angular view showing a partial disassembly of an orthodontic appliance relating to Example 1 of the present invention.

The present orthodontic appliance mounts a memory alloy coil spring having superelastic properties previously set at a desired load between a pair of bases. When used for treatment for expansion of the upper jaw bone and treatment for alveolar shifting of teeth, the spring force of the superelastic coil spring is transmitted to the teeth and to the jaw bone by means of the pair of bases shifting in the opening direction or in the closing direction. In the course of such treatment, even for example when shifting of the teeth and expansion of the upper jaw bone are in process, it becomes possible to transmit a constantly fixed orthodontic force continuously to the teeth. Because of this, the prior need to adjust the orthodontic force during course of treatment is primarily eliminated in that it is possible to perform such treatment for expansion of the upper jaw bone and treatment for shifting of teeth continuously under the ideal orthodontic force.

Example 1

The present device will next be explained based on examples illustrated in the drawings. Example 1 uses a compression coil spring formed from a material such as Ni-Ti type alloy wire material.

Figure 2:
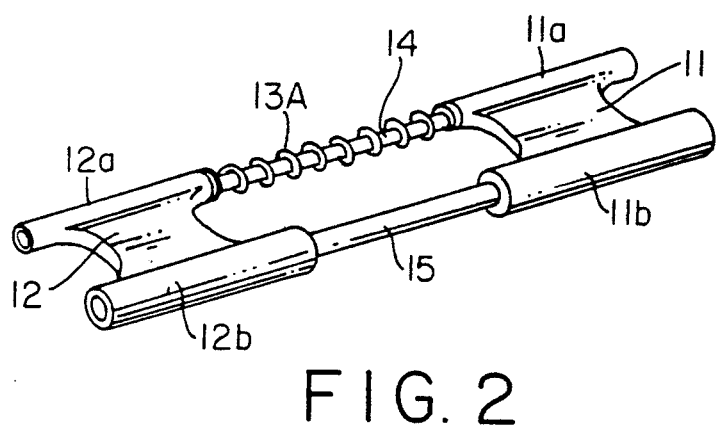
FIG. 2 is an angular view showing the same orthodontic appliance of FIG. 1 assembled.
Figure 3:
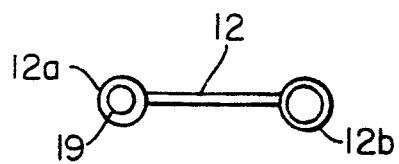
FIG. 3 is a cross sectional view of the base 12 of the appliance illustrated in FIG. 1.

To explain this embodiment, as shown in FIGS. 1 and 2, pair of bases 11 and 12 form a near H-shape having tubular parts on both sides. A retention rod 14 retains the superelastic compression coil spring 13A. Retention rod 14 is held in tubular part 11a on one side of the said base 11. The tip of the retention rod 14 inserts into tubular part 12a on one side of the other opposing base 12. By engaging and stopping tip expansion head 14a of retention rod 14 with a stopper 19 (see FIG. 3) furnished inside the tubular part 12a, base 12 is prevented from coming off retention rod 14. At the same time guide rod 15 is inserted into tubular parts 11b and 12b on the other sides of the two bases 11 and 12, giving a construction wherein base 12 is supported so as to be openable 16 and closable relative to the other base 11 by the guide action of the retention rod 14 and the guide rod 15. One end of the guide rod 15 may be permanently fixed into tubular part 12b or tubular part 11b while the opposite end of the rod 15 is slidably received in the other tubular part. The end of retention rod 14 opposite the head 14a may also be permanently fixed within tubular part 11a as illustrated in FIG. 1. Alternatively, both ends of guide rod 15 and retention rod 14 may be slidably received within the tubular parts.

Figure 4:
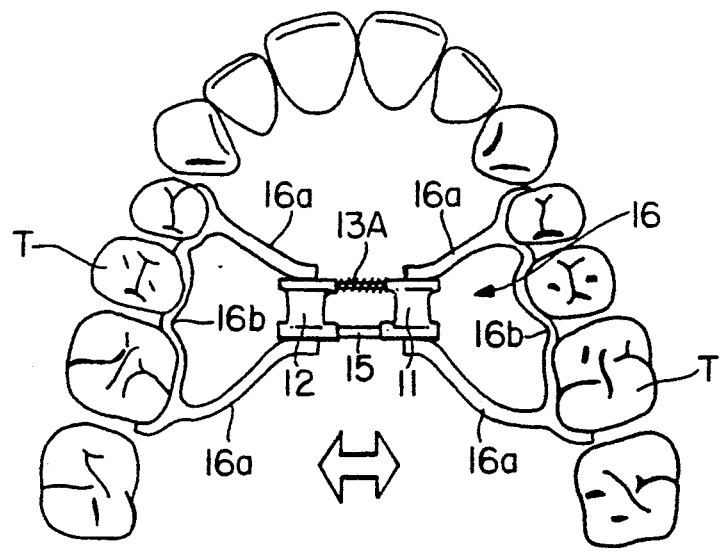
FIG. 4 is an explanatory diagram showing an example of expansion treatment of the upper jaw bone using the orthodontic appliance of FIG. 1.
Figure 5:
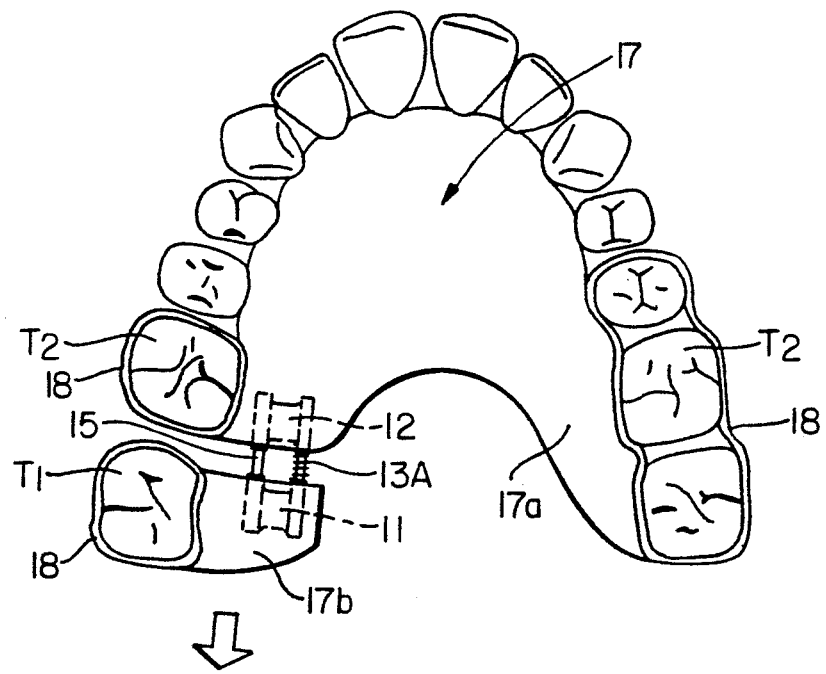
FIG. 5 is an explanatory diagram showing an example of treatment for shifting teeth.

When using the orthodontic appliance of Example 1 in treatment for expansion of the upper jaw bone, the pair of bases 11 and 12 are set with a jig or the like to a position where they approach one another following the spring pressure of superelastic compression coil spring 13A (this is not illustrated), and as shown in FIG. 4 the pair of bases 11 and 12 are soldered to connecting arms 16a of fixed type expansion apparatus 16 in the conventional manner. After attaching the sides 16b of the expansion apparatus 16 to the surfaces of teeth T by means of adhesive or bands (not illustrated) and removing the said jig, base 12 shifts along retention rod 14 and guide rod 15 in the direction where it moves away from base 11 by the spring action of superelastic compression coil spring 13A. Spring 13A thus transmits an orthodontic force to teeth T and T on both sides of the mouth, thereby making it possible to shift the patient's tooth T1 in the prescribed direction. It is understood that tooth T1 is not restricted to being one tooth, but may also be multiple teeth.

Since the present invention utilizes superelastic compression coil spring 13A instead of the prior threaded rod, it is possible to impart a substantially constant predetermined orthodontic force to the side of tooth continuously during the course of treatment, within the range of superelasticity, even though expansion of the upper jaw bone and shifting of teeth are in process. Because of this, there is no need to adjust the orthodontic force frequently during the course of treatment as was the case before the present invention.

Example 2

Figure 6:
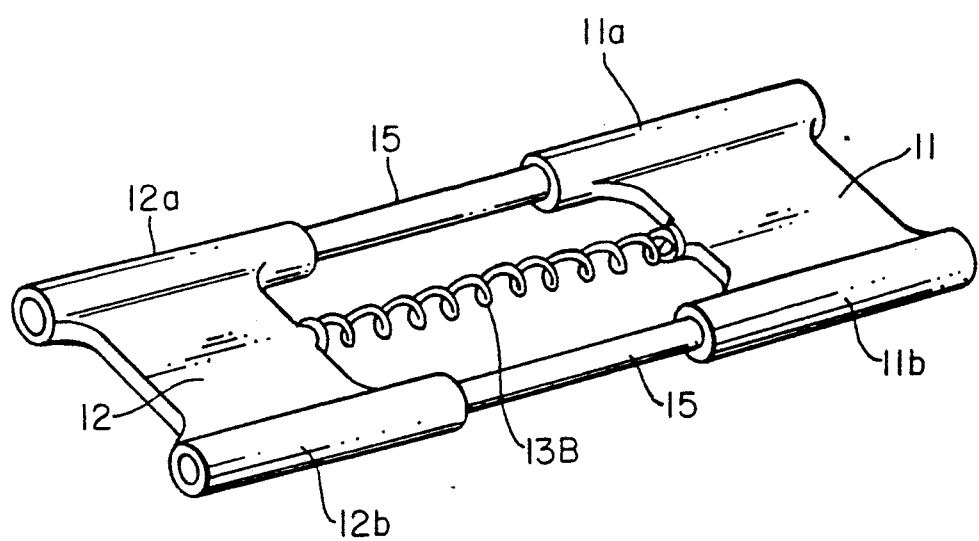
FIG. 6 is an angular view showing an orthodontic appliance pertaining to Example 2.
Figure 7:
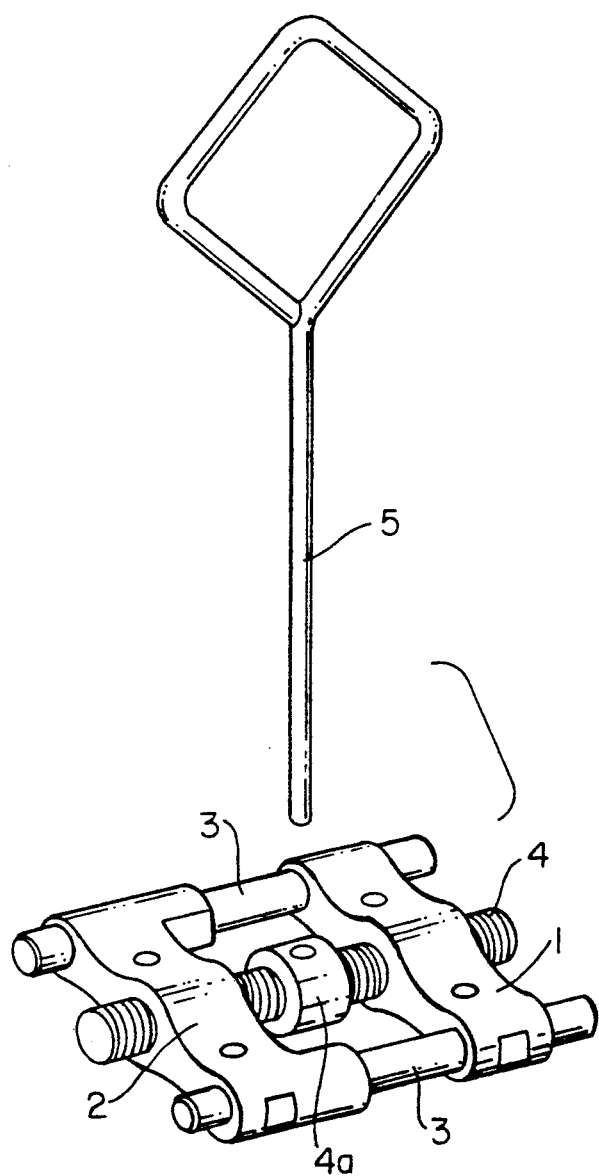
FIG. 7 is an angular view showing a prior art orthodontic appliance.
Figure 8:
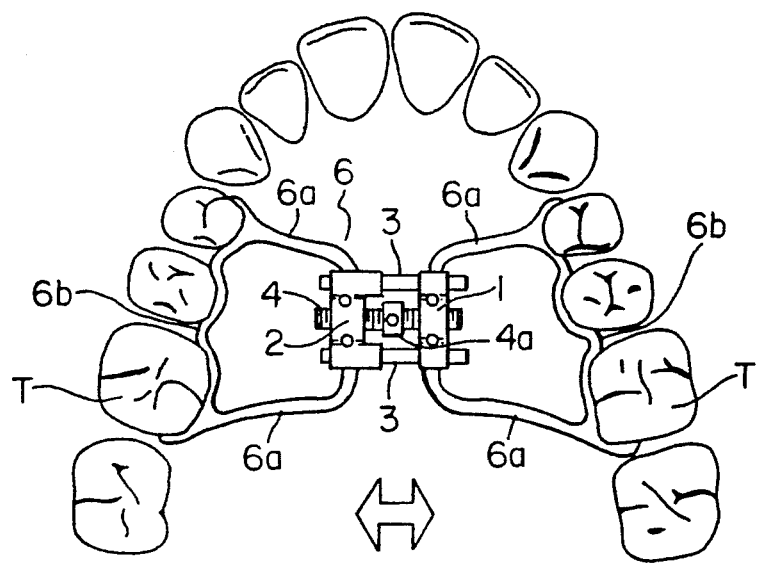
FIG. 8 is an explanatory diagram showing an example of expansion treatment of the upper jaw bone using the orthodontic appliance of FIG. 7.
Figure 9:
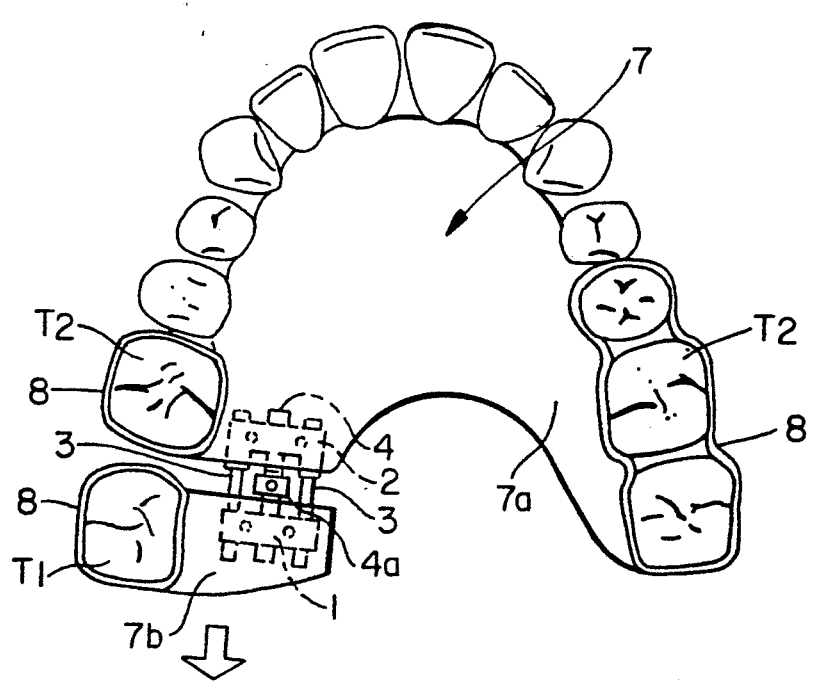
FIG. 9 is an explanatory diagram showing an example of treatment for shifting teeth.

Example 2 of the present invention will be explained next. An orthodontic appliance pertaining to this example uses a tension superelastic coil spring formed from, for example, Ni-Ti type alloy wire material as the superelastic coil spring. This embodiment as shown in FIG. 6 has two guide rods 15 respectively inserted into cylinder parts 11a, 11b, 12a and 12b on the sides of the pair of bases 11 and 12. Base 12 is supported so as to be openable or closable relative to the opposite base 11 in the same manner as Example 1. The superelastic tensile coil spring 13B is mounted in the central parts of the bases 11 and 12.

The orthodontic appliance of Example 2 differs from Example 1 in the mounting of superelastic tension coil spring 13B. This embodiment makes possible a treatment for contraction of the upper jaw bone and inverted shifting of teeth. In these cases as well, the spring pressure obtained from the superelasticity of tension coil spring 13B is directly transmitted to the side of the tooth by means of pair of bases 11 and 12, making it possible to impart a substantially constant fixed orthodontic force continually. Because of this, there is no need to adjust the orthodontic force frequently during the course of treatment as was the case before this invention. Furthermore, it is possible to perform such a treatment for contraction of the upper jaw bone and treatment for shifting of teeth while constantly under the predetermined orthodontic force.

Further, when setting the product of this Example 2 in a fixed type contraction apparatus and removable bed apparatus, as shown in the drawing the pair of bases 11 and 12 are assembled into each apparatus by setting them in a state where they are separated by a jig (not illustrated) or the like counter to the spring force of tension coil spring 13, which is the reverse of Example 1. When the orthodontic appliance is released from the jig at the start of treatment, the spring pressure of tension coil spring 13B can then be transmitted directly to the side of the tooth.

As stated above, the present invention is characterized in that a superelastic coil spring is mounted between a pair of bases which transmit the pressure of the superelastic coil spring as an orthodontic force to the tooth or jaw bone by means of a pair of bases that move together or apart. Because of this, it is possible to transmit a substantially constant fixed orthodontic force continually to the teeth and the upper jaw bone by effectively utilizing the superelasticity of the coil spring even if expansion of the upper jaw bone and shifting of teeth is underway in the course of treatment, so that the need to regulate orthodontic force frequently during the course of treatment is now eliminated.

What is claimed is:

1. An orthodontic appliance for shifting teeth comprising:
    a first pair of parallel tubular members which are joined in fixed relationship at sides thereof, each tubular member having an open end;
    a second pair of parallel tubular members which are joined in fixed relationship at sides thereof, each tubular member having an open end which opposes an open end of the first pair of tubular members;
    a guide rod slidably received within an open end of a tubular member of one of said pairs and received within the opposing open end of a tubular member of the other pair;
    a retention rod slidably received within an open end of a tubular member of one of said pairs and received within the opposing open end of a tubular member of the other pair, whereby said first pair and second pair of tubular members are capable of sliding movement in the longitudinal direction toward each other and away from each other; and a memory alloy coil spring disposed around said retention rod so as to be capable of longitudinal compression in response to movement of the first and second pair of tubular members toward each other so as to exert a substantially constant expansive longitudinal force on the first and second pair of tubular members when compressed.

2. The orthodontic appliance according to claim 1 wherein the parallel tubular members of each pair are joined in fixed relationship at sides thereof by a planar web.

3. The orthodontic appliance according to claim 1 wherein the retention rod is fixedly received within said opposing open end of a tubular member of the other pair.

4. The orthodontic appliance according to claim 3 wherein the guide rod is slidably received within said opposing open end of a tubular member of the other pair.

5. The orthodontic appliance according to claim 3 wherein the guide rod is fixedly received within said opposing open end of a tubular member of the other pair.

6. The orthodontic appliance according to claim 1 wherein the retention rod is slidably received within said opposing open end of a tubular member of the other pair.

7. The orthodontic appliance according to claim 6 wherein the guide rod is slidably received within said opposing open end of a tubular member of the other pair.

8. The orthodontic appliance according to claim 6 wherein the guide rod is fixedly received within said opposing open end of a tubular member of the other pair.

9. The orthodontic appliance according to claim 1 further comprising means for limiting movement of the first and second pair of tubular members away from each other in the longitudinal direction so that the guide rod and retention rod remain permanently received within opposing tubular members.

10. The orthodontic appliance according to claim 9 wherein the means for limiting comprises a stop member disposed within the tubular member which slidably receives the retention rod and a cooperating head on an end of the retention rod received within the tubular member having the stop member, the head being incapable of sliding past the stop member in the longitudinal direction.

11. The orthodontic appliance according to claim 1 wherein the coil spring comprises superelastic nickel titanium alloy.

12. The orthodontic appliance according to claim 1 further comprising means for coupling each pair of tubular members to teeth.

13. The orthodontic appliance according to claim 1 wherein the coil spring has two opposite ends which are attached to the opposing tubular members so that the spring can be expanded in the longitudinal direction in response to longitudinal movement of the opposing tubular members away form each other so as to exert a contractive force on said opposing tubular members.

14. An orthodontic appliance for continuously transmitting an orthodontic force to teeth or a jaw without the need for adjustment to accommodate for the shifting of the teeth or contraction or expansion of the jaw comprising:

a pair of opposing bases, each base including a pair of parallel tubular members which are separated and joined by a planar web;

a pair of guide rods for coupling and guiding said opposing bases for linear sliding movement in a longitudinal direction toward each other and away from each other, each guide rod having two opposite ends which are slidably received within tubular members of opposing bases; and memory alloy spring means having superelastic properties attached between the opposing bases, each spring means capable of longitudinal expansion in response to longitudinal movement of the opposing bases away from each other so as to exert a contractive longitudinal force on the bases when expanded.

15. The orthodontic appliance according to claim 14 wherein the spring means is a superelastic coil spring having two opposite ends attached to central portions of the planar webs of opposing bases.

16. The orthodontic appliance according to claim 15 wherein the superelastic coil spring is constructed of a nickel titanium alloy.

17. The orthodontic appliance according to claim 14 further comprising retaining means for said spring means so that the spring means is capable of longitudinal compression in response to longitudinal movement of opposing bases toward each other so as to exert an expansive longitudinal force on the bases when compressed.

* * * * *

UNITED STATES PATENT AND TRADEMARK OFFICE
CERTIFICATE OF CORRECTION

PATENT NO. : 5,167,500

DATED : December 1, 1992

INVENTOR(S) : Fujio MIURA

It is certified that error appears in the above-identified patent and that said Letters Patent is hereby corrected as shown below:

Column 3, line 21, delete "16".

Column 6, line 12, change "form" to --from--.

Column 6, line 29, change "each" to --said--.

Signed and Sealed this

Ninth Day of November, 1993

Attest:

BRUCE LEHMAN

*Attesting Officer*

*Commissioner of Patents and Trademarks*